(12) United States Patent
Yao et al.

(10) Patent No.: US 11,865,538 B2
(45) Date of Patent: Jan. 9, 2024

(54) BIOLOGICAL DETECTION CHIP, BIOLOGICAL DETECTION DEVICE, AND DETECTION METHOD THEREOF

(71) Applicants: BEIJING BOE OPTOELECTRONICS TECHNOLOGY CO., LTD., Beijing (CN); BOE TECHNOLOGY GROUP CO., LTD., Beijing (CN)

(72) Inventors: Wenliang Yao, Beijing (CN); Nan Zhao, Beijing (CN); Peizhi Cai, Beijing (CN); Fengchun Pang, Beijing (CN); Yue Geng, Beijing (CN); Le Gu, Beijing (CN); Yuelei Xiao, Beijing (CN); Hui Liao, Beijing (CN); Yingying Zhao, Beijing (CN); Bolin Fan, Beijing (CN)

(73) Assignees: BEIJING BOE OPTOELECTRONICS TECHNOLOGY CO., LTD., Beijing (CN); BOE TECHNOLOGY GROUP CO., LTD., Beijing (CN)

( * ) Notice: Subject to any disclaimer, the term of this patent is extended or adjusted under 35 U.S.C. 154(b) by 444 days.

(21) Appl. No.: 16/757,902

(22) PCT Filed: Mar. 27, 2019

(86) PCT No.: PCT/CN2019/079899
§ 371 (c)(1),
(2) Date: Apr. 21, 2020

(87) PCT Pub. No.: WO2020/191672
PCT Pub. Date: Oct. 1, 2020

(65) Prior Publication Data
US 2021/0162409 A1 Jun. 3, 2021

(51) Int. Cl.
*B01L 3/00* (2006.01)
*G01N 33/487* (2006.01)
*H01L 27/12* (2006.01)

(52) U.S. Cl.
CPC .. *B01L 3/502715* (2013.01); *G01N 33/48707* (2013.01); *H01L 27/1214* (2013.01);
(Continued)

(58) Field of Classification Search
CPC ....... B01L 3/502715; B01L 2300/0819; B01L 2300/0645; B01L 2300/0663; B01L 2300/0816; G01N 33/48707; G01N 33/48
See application file for complete search history.

(56) References Cited

U.S. PATENT DOCUMENTS

2004/0053451 A1* 3/2004 Ono ................. H01L 29/78627
438/164
2009/0299213 A1 12/2009 Patolsky et al.
(Continued)

FOREIGN PATENT DOCUMENTS

CN 1926428 3/2007
CN 101181158 5/2008
(Continued)

OTHER PUBLICATIONS

Translation of CN102520044A, Zhaoxia Shi, Jun. 27, 2012 (Year: 2012).*
Shaik et al., "Thin-film-transistor array: an exploratory attempt for high throughput cell manipulation using electrowetting principle", J. Micromech. Microeng., 2017, 27, 054001 (Year: 2017).*
Eversmann et al., "A 128x128 CMOS Biosensor Array for Extracellular Recording of Neural Activity", IEEE journal of Solid-State Circuits, vol. 38, No. 12, 2003 (Year: 2003).*

*Primary Examiner* — Samuel P Siefke
*Assistant Examiner* — Henry H Nguyen
(74) *Attorney, Agent, or Firm* — Leason Ellis LLP

(57) ABSTRACT

A biological detection chip, a biological detection device, and a detection method thereof are disclosed. The biological detection chip includes a first base substrate and a plurality of detection units arranged in an array along a row direction and a column direction on the first base substrate. Each of the plurality of detection units includes a thin film transistor
(Continued)

and an electrode, the thin film transistor is on the first base substrate and includes a gate electrode, a source electrode, and a drain electrode, and the electrode is on a side of the thin film transistor away from the first base substrate and is connected to the drain electrode, and the electrode is configured to carry a biological material to be detected.

17 Claims, 3 Drawing Sheets

(52) U.S. Cl.
CPC .................. *B01L 2300/0645* (2013.01); *B01L 2300/0819* (2013.01)

(56) References Cited

U.S. PATENT DOCUMENTS

| | | |
|---|---|---|
| 2010/0248284 A1 | 9/2010 | Chen et al. |
| 2017/0358601 A1* | 12/2017 | Kim .................... H01L 27/1203 |

FOREIGN PATENT DOCUMENTS

| | | |
|---|---|---|
| CN | 201269873 | 7/2009 |
| CN | 102279217 | 12/2011 |
| CN | 102520044 | 6/2012 |
| CN | 107356649 | 11/2017 |
| WO | 2016172623 | 10/2016 |

* cited by examiner

BIOLOGICAL DETECTION CHIP, BIOLOGICAL DETECTION DEVICE, AND DETECTION METHOD THEREOF

CROSS-REFERENCE TO RELATED PATENT APPLICATIONS

This application is a U.S. National Stage Application under 35 U.S.C. § 371 of International Patent Application No. PCT/CN2019/079899, filed Mar. 27, 2019, which is incorporated by reference in its entirety.

TECHNICAL FIELD

The embodiments of the present disclosure relate to a biological detection chip, a biological detection device, and a detection method thereof.

BACKGROUND

Microfluidics technology is a technology that can manipulate or detect fluids at the micrometer scale. Microfluidic technology has the ability to miniaturize the basic functions of biological, chemical, and other laboratories onto a chip of a few square centimeters, so that basic operations such as sample preparation, reaction, separation, and detection during a biochemical analysis process can be completed automatically. Micro-electro-mechanical systems (MEMS) technology is a new discipline developed on the basis of microelectronics and micro-machining, and is playing an increasingly important role in a field of biological detection.

Nerve cells, also called neurons, are the basic structural and functional units that make up the mammalian nervous system. Structurally, neurons are divided into two parts: soma and neurites. The neurite is divided into a dendrite and an axon. The dendrite mostly shows dendritic branches and can receive stimuli and transmit impulses to the soma; the axon mostly shows slender shape and have fewer branches, and can achieve impulse conduction. Generally, each neuron includes one or more dendrites, but only one axon. The transmission of impulses between neurons mainly depends on synapses, and a large number of neurons contact each other through synapses to form the nervous system.

Generally, the synapse includes two membrane layers, and the two membrane layers are called presynaptic membrane and postsynaptic membrane (thickness ranging from 7 to 10 nanometers), there is a synaptic gap (20-30 nanometers) between the presynaptic membrane and the postsynaptic membrane. In a case where the impulse of the presynaptic neuron reaches the synaptosome, neurotransmitters in the synaptic vesicle are released from the presynaptic membrane, enters the synaptic gap, and acts on the postsynaptic membrane. In a case where the chemical effect exceeds a certain threshold, it can cause excitatory response or inhibition response in the postsynaptic neurons, thereby transmitting the impulses to the postsynaptic neurons.

SUMMARY

An embodiment of the present disclosure provides a biological detection chip, a biological detection device, and a detection method thereof. The biological detection chip comprises: a first base substrate; and a plurality of detection units arranged in an array along a row direction and a column direction on the first base substrate. Each of the plurality of detection units comprises a thin film transistor and an electrode, the thin film transistor is on the first base substrate and comprises a gate electrode, a source electrode, and a drain electrode, and the electrode is on a side of the thin film transistor away from the first base substrate and is connected to the drain electrode, and the electrode is configured to carry a biological material to be detected. Thus, the biological detection chip can reduce the complexity of the routing of the plurality of detection units, thereby increasing the density of the plurality of detection units, furthermore achieving flexible control of electrical stimulation and impulse detection at different positions of the biological material to be detected (such as nerve cells). On the other hand, the biological detection chip can also increase the effective area for culturing and detecting the biological material to be detected, and can avoid the electrical stimulation process of the biological material to be detected from interfering the gate lines and the data lines.

At least one embodiment of the present disclosure provides a biological detection chip, and the biological detection chip includes: a first base substrate; and a plurality of detection units arranged in an array along a row direction and a column direction on the first base substrate. Each of the plurality of detection units comprises a thin film transistor and an electrode, the thin film transistor is on the first base substrate and comprises a gate electrode, a source electrode, and a drain electrode, and the electrode is on a side of the thin film transistor away from the first base substrate and is connected to the drain electrode, and the electrode is configured to carry a biological material to be detected.

For example, the biological detection chip provided by an embodiment of the present disclosure further includes: a plurality of gate lines; and a plurality of data lines arranged to intersect the plurality of gate lines. Each of the plurality of gate lines and the gate electrodes of the detection units in a same row are connected and are on a same layer, and each of the plurality of data lines and the source electrodes of the detection units in a same column are connected and are on a same layer.

For example, in the biological detection chip provided by an embodiment of the present disclosure, the plurality of detection units comprise stimulation units and receiving units, the stimulation units are configured to apply stimulation voltages, and the receiving units are configured to receive electrophysiological signals.

For example, in the biological detection chip provided by an embodiment of the present disclosure, in the row direction, the stimulation units and the receiving units are alternately arranged, and one stimulation unit and one receiving unit, which are adjacent, are axisymmetric with respect to a separation line between the one stimulation unit and the one receiving unit, which are adjacent.

For example, in the biological detection chip provided by an embodiment of the present disclosure, in the column direction, the stimulation units and the receiving units are alternately arranged, and two stimulation units and two receiving units constitute a detection point, and in the detection point, orthographic projections of the two stimulation units on the first base substrate and orthographic projections of the two receiving units on the first base substrate form a 2*2 matrix.

For example, in the biological detection chip provided by an embodiment of the present disclosure, an orthographic projection of the detection point on the first base substrate is substantially a rectangle, and a side length of the rectangle ranges from 4 to 6 microns.

At least one embodiment of the present disclosure further provides a biological detection device, and the biological detection device comprises: the biological detection chip according to any one of the above embodiments; and an opposite substrate, cell-assembled with the biological detection chip to form a culture cavity between the biological detection chip and the opposite substrate.

For example, in the biological detection device provided by an embodiment of the present disclosure, the opposite substrate comprises: a second base substrate; a breathable film, on a side of the second base substrate away from the biological detection chip; and a cover plate, on a side of the breathable film away from the second base substrate. The cover plate and the breathable film are spaced apart to form a gas channel between the cover plate and the breathable film, and the second base substrate is provided with a vent hole, and an orthographic projection of the vent hole on the second base substrate is located within an orthographic projection of the gas channel on the second base substrate.

For example, the biological detection device provided by an embodiment of the present disclosure further includes: a plurality of support members, between the biological detection chip and the opposite substrate and surrounding the plurality of detection units. The plurality of support members are spaced apart to form a liquid flow channel that is between adjacent ones of the plurality of support members and in communication with the culture cavity.

For example, the biological detection device provided by an embodiment of the present disclosure further includes: a reagent module, which is in communication with the culture cavity through the liquid flow channel. The reagent module comprises at least two reagent reservoirs and a reagent mixing region, the at least two reagent reservoirs are configured to store different types of detection reagents, and the reagent mixing region is configured to mix different types of detection reagents.

For example, in the biological detection device provided by an embodiment of the present disclosure, the reagent mixing region further comprises a fish-bone mixing structure.

At least one embodiment of the present disclosure further provides a biological detection method of a biological detection device, wherein the biological detection device is the above-mentioned biological detection device, and the biological detection method comprises: cultivating the biological material to be detected on the electrode on the biological detection chip, the biological material to be detected covering at least part of the detection units; cell-assembling the biological detection chip and the opposite substrate; introducing a detection reagent into the culture cavity; and using the detection units covered by the biological material to be detected to detect an influence of the detection reagent on the biological material to be detected.

For example, in the biological detection method provided by an embodiment of the present disclosure, the opposite substrate comprises: a second base substrate; a breathable film, on a side of the second base substrate away from the biological detection chip; and a cover plate, on a side of the breathable film away from the second base substrate; the cover plate and the breathable film are spaced apart to form a gas channel between the cover plate and the breathable film, and the second base substrate is provided with a vent hole, and an orthographic projection of the vent hole on the second base substrate is located within an orthographic projection of the gas channel on the second base substrate; the biological detection method further comprises: introducing gas into the gas channel; and using the detection units covered by the biological material to be detected to detect an influence of the gas on the biological material to be detected.

For example, in the biological detection method provided by an embodiment of the present disclosure, the detection units covered by the biological material to be detected comprise a first detection point located at a stimulation position of the biological material to be detected and a second detection point located at a receiving position of the biological material to be detected, and using the detection units covered by the biological material to be detected to detect the influence of the detection reagent on the biological material to be detected comprises: applying electrical stimulation to the stimulation position of the biological material to be detected by the first detection point; and receiving an electrophysiological signal at the receiving position of the biological material to be detected by the second detection point. The first detection point comprises at least one of the detection units, and the second detection point comprises at least one of the detection units.

For example, in the biological detection method provided by an embodiment of the present disclosure, the detection units covered by the biological material to be detected comprises a first detection point located at a stimulation position of the biological material to be detected and a second detection point located at a receiving position of the biological material to be detected, and using the detection units covered by the biological material to be detected to detect the influence of the gas on the biological material to be detected comprises: applying electrical stimulation to the stimulation position of the biological material to be detected by the first detection point; and receiving an electrophysiological signal at the receiving position of the biological material to be detected by the second detection point. The first detection point comprises at least one of the detection units, and the second detection point comprises at least one of the detection units.

For example, in the biological detection method provided by an embodiment of the present disclosure, the biological material to be detected comprises at least one nerve cell, the stimulation position of the biological material to be detected comprises a dendrite of a nerve cell, and the receiving position of the biological material to be detected comprises an axon or a myelin sheath of a nerve cell at the stimulation position, or an axon or a myelin sheath of another nerve cell connected to the nerve cell at the stimulation position.

For example, the biological detection method provided by an embodiment of the present disclosure further includes: acquiring an image of the biological material to be detected on the biological detection chip; determining, according to the image, the detection units covered by the biological material to be detected and a positional relationship between the detection units and the biological material to be detected; and determining the first detection point and the second detection point according to the positional relationship between each of the detection units and the biological material to be detected

BRIEF DESCRIPTION OF THE DRAWINGS

In order to clearly illustrate the technical solutions of the embodiments of the disclosure, the drawings of the embodiments will be briefly described in the following; it is obvious that the described drawings are only related to some embodiments of the disclosure and thus are not limitative to the disclosure.

DETAILED DESCRIPTION

Figure 1:
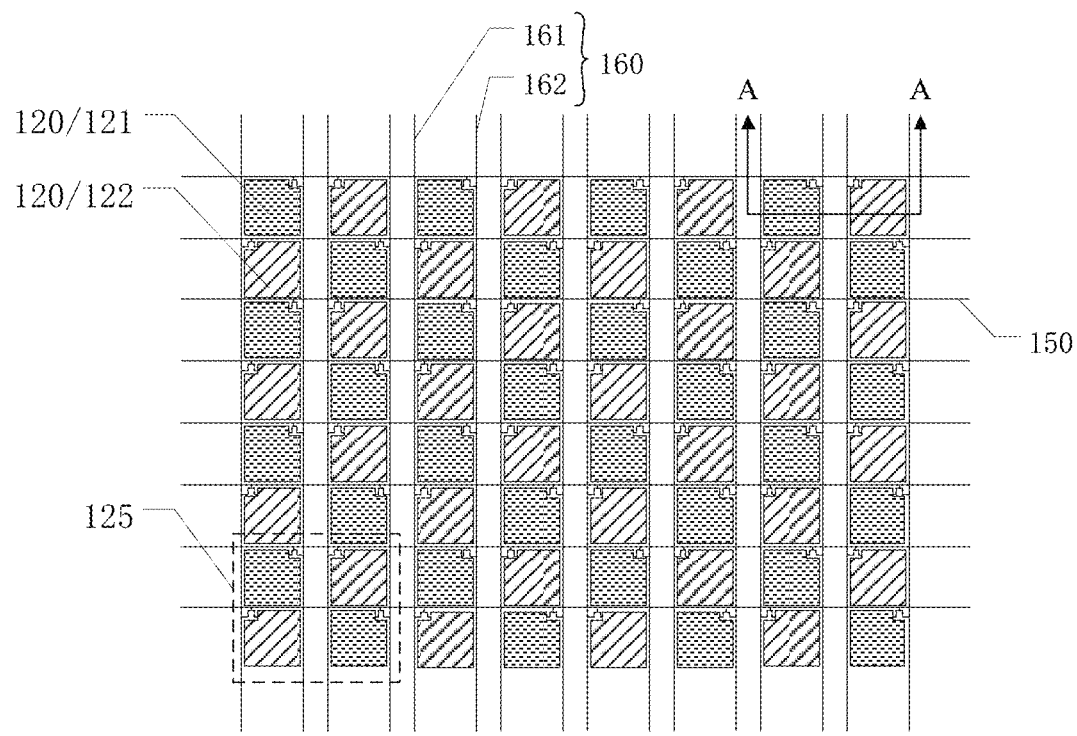
FIG. 1 is a schematic plane diagram of a biological detection chip according to an embodiment of the present disclosure.

In order to make objects, technical details and advantages of the embodiments of the disclosure apparent, the technical solutions of the embodiments will be described in a clearly and fully understandable way in connection with the drawings related to the embodiments of the disclosure. Apparently, the described embodiments are just a part but not all of the embodiments of the disclosure. Based on the described embodiments herein, those skilled in the art can obtain other embodiment(s), without any inventive work, which should be within the scope of the disclosure.

Unless otherwise defined, all the technical and scientific terms used herein have the same meanings as commonly understood by one of ordinary skill in the art to which the present disclosure belongs. The terms "first," "second," etc., which are used in the present disclosure, are not intended to indicate any sequence, amount or importance, but distinguish various components. The terms "comprise," "comprising," "include," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly.

The impulse transmission of the nerve cell is mainly achieved through an electrochemical process. In a case where the nerve cell is not stimulated, a stable potential difference, which is called a transmembrane resting potential, is maintained on two sides of the cell membrane. In this case, a potential inside the cell membrane is low and a potential outside the cell membrane is high, and a range of the potential difference varies in tens of millivolts. In a case where the nerve cell is stimulated by the external electrophysiological signal, the ion permeability of the cell membrane changes sharply, so that the potential difference between the two sides of the cell membrane changes, and the potential difference formed with the adjacent cell membrane causes the potential to propagate sequentially, thereby achieving the transmission of impulses along the nerve cells.

Therefore, the effects of different types of detection reagents, different concentrations of detection reagents, different types of gases, and different concentrations of gases on nerve cells and nervous systems can be detected using a micro-electrode array (MEA) sensor. Generally, the micro-electrode array (MEA) sensor includes a base substrate and a micro-electrode array on the base substrate. In a case where the nerve cells or tissues are cultured on the surface of the micro-electrode array sensor, an externally applied electrical stimulation signal (such as, a pulse voltage) can be transmitted to the micro-electrodes, thereby stimulating the nerve cells and causing the nerve cells to generate impulses, and other micro-electrodes record the electrophysiological signals of different positions of the nerve cells or the electrophysiological signals of other nerve cells to achieve the research of the nerve cells or tissues.

However, due to the randomness of adherent growth of nerve cells, the synaptic connection manners and growth positions of different nerve cells are very different; and the connection manner between nerve cells in each cell culture is also random. The positions of the micro-electrodes on the micro-electrode array (MEA) sensor are relatively fixed, thereby making it impossible for researchers to perform electrical stimulation and impulse detection on the neurons in specific positions, which is not easy to evaluate the regularity of neural cell communication and the effectiveness of the nervous system constructed by nerve cells. On the other hand, each micro-electrode on a conventional micro-electrode array (MEA) sensor is connected and controlled by a separate wiring, which increases the complexity of the wiring, thus restricting the number of micro-electrode arrays and reducing the effective cultivation area. In addition, the conventional micro-electrode array (MEA) sensor can only use specific conditions to culture nerve cells or the nervous system constructed by the nerve cells. It cannot achieve flexible control of the culture environment, and it is not easy to study the influence of different detection reagents, different detection reagent concentrations, different gases, and different gas concentrations on the function of the nerve cells or the nervous system, thereby having large limitations.

An embodiment of the present disclosure provides a biological detection chip, a biological detection device, and a detection method thereof. The biological detection chip comprises: a first base substrate; and a plurality of detection units arranged in an array along a row direction and a column direction on the first base substrate. Each of the plurality of detection units comprises a thin film transistor and an electrode, the thin film transistor is on the first base substrate and comprises a gate electrode, a source electrode, and a drain electrode, and the electrode is on a side of the thin film transistor away from the first base substrate and is connected to the drain electrode, and the electrode is configured to carry a biological material to be detected. Because each detection unit includes a thin film transistor and an electrode, the plurality of detection units can be individually driven by the gate lines provided along the row direction and the data lines provided along the column direction; in addition, because the gate electrode, the source electrode and the drain electrode, and the electrode are located in different layers, the gate lines and the data lines for driving the plurality of detection units may be disposed at different layers from the electrode. Thus, the biological detection chip can reduce the complexity of the routing of the plurality of detection units, thereby increasing the density of the plurality of detection units, increasing the number of detection units per unit area, furthermore achieving flexible control of electrical stimulation and impulse detection at different positions of the biological material to be detected (such as nerve cells). On the other hand, the biological detection chip can also increase the effective area for culturing and detecting the biological material to be detected, and can avoid the electrical stimulation process of the biological material to be detected from interfering the gate lines and the data lines.

Hereinafter, the biological detection chip, the biological detection device, and the detection method thereof provided in the embodiments of the present disclosure will be described in detail with reference to the accompanying drawings.

Figure 2:
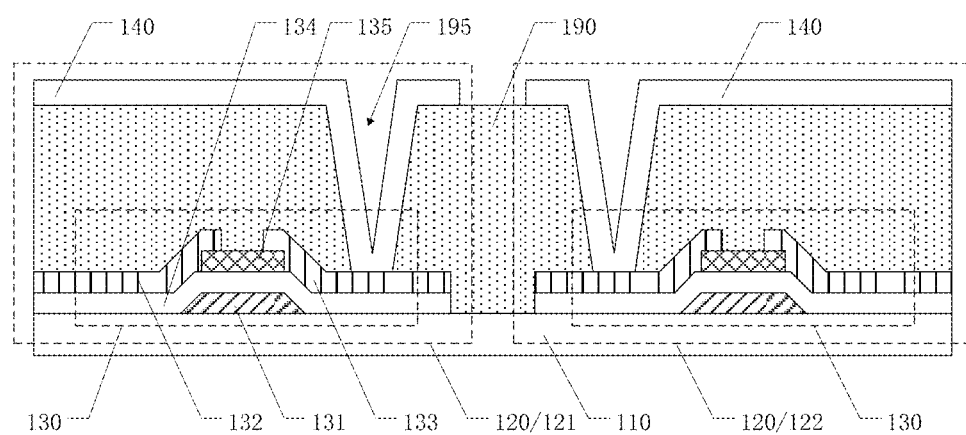
FIG. 2 is a schematic cross-sectional view of a biological detection chip along an AA direction in FIG. 1 according to an embodiment of the present disclosure.

An embodiment of the present disclosure provides a biological detection chip. FIG. 1 is a schematic plane diagram of a biological detection chip according to an embodiment of the present disclosure; FIG. 2 is a schematic cross-sectional view of a biological detection chip along an AA direction in FIG. 1 according to an embodiment of the present disclosure. As illustrated by FIG. 1, the biological detection chip includes a first base substrate 110 and a plurality of detection units 120. The plurality of detection units 120 are arranged in an array in a row direction and a column direction on the first base substrate 110. As illustrated by FIG. 2, each detection unit 120 includes a thin film transistor 130 and an electrode 140. The thin film transistor 130 is disposed on the first base substrate 110 and includes a gate electrode 131, a source electrode 132, and a drain electrode 133. The electrode 140 is disposed on a side of the thin film transistor 130 away from the first base substrate 110 and is connected to the drain electrode 133. The electrode 140 may carry a biological material to be detected, for example, the biological material to be detected may be cultured on the electrode 140.

For example, as illustrated by FIG. 2, the thin film transistor 130 further includes a gate insulating layer 134 and an active layer 135; the gate electrode 131 is disposed on the first base substrate 110, and the gate insulating layer 134 is disposed on a side of the gate electrode 131 away from the first base substrate 110, the active layer 135 is disposed on a side of the gate insulating layer 134 away from the gate electrode 131 and is opposite to the gate electrode 131 (for example, the orthographic projection of the active layer 135 on the first base substrate 110 covers the orthographic projection of the gate electrode 131 on the first base substrate 110), the source electrode 132 and the drain electrode 133 are located on a side of the gate insulating layer 134 and the active layer 135 away from the gate electrode 131. The biological detection chip further includes a passivation layer 190, and the passivation layer 190 is located on a side of the thin film transistor 130 away from the first base substrate 110. The electrode 140 can be electrically connected to the drain electrode 133 through a hole 195 in the passivation layer 190. It can be seen that the gate electrode 131, the source electrode 132, and the drain electrode 133 of the thin film transistor 130, and the electrode 140 are located in different layers.

In the biological detection chip provided by the embodiment of the present disclosure, because each detection unit includes a thin film transistor and an electrode, the plurality of detection units can be individually driven by the gate lines provided along the row direction and the data lines provided along the column direction, thereby reducing the number and complexity of the routing of the plurality of detection units. For example, in a case where a biological detection chip has 8*8 detection units, a general biological detection chip needs to be provided with 8*8 signal lines to drive the above 8*8 detection units, respectively; however, the biological detection chip provided in the embodiment of the present disclosure can drive 8*8 detection units by only providing (8+8) or (8+16) signal lines. Therefore, the biological detection chip can reduce the number and complexity of the routing of the plurality of detection units, thereby increasing the density of the plurality of detection units (the area for the routing in a unit area is reduced, and the density of the detection units can be increased), and furthermore achieving flexible control of electrical stimulation and impulse detection at different positions of the biological material to be detected. For example, in a case where the biological material to be detected is a nerve cell, if the density of the plurality of detection units increases, the number of detection units covered by the nerve cell will increase, so that the electrical stimulation and the impulse detection can be performed on more positions of the nerve cell, thereby improving the accuracy of detection.

On the other hand, because the gate electrode, the source electrode and the drain electrode, and the electrode are located in different layers, the gate lines and data lines used to drive the plurality of detection units can be disposed at different layers from the electrode, in this case, the orthographic projections of the gate lines and the data lines on the first base substrate is also close to or even overlapped with the orthographic projection of the electrode on the first base substrate. Therefore, the biological detection chip can further increase the density of the plurality of detection units (increasing the number of detection units per unit area), and further improve the degree of flexible control of electrical stimulation and impulse detection at different positions of the biological material to be detected (such as nerve cells). In addition, the biological detection chip can also increase the effective area for culturing and detecting the biological material to be detected, and can avoid the electrical stimulation process of the biological material to be detected from interfering the gate lines and the data lines.

For example, in some examples, as illustrated by FIG. 1, the biological detection chip further includes a plurality of gate lines 150 and a plurality of data lines 160; the plurality of gate lines 150 and the plurality of data lines 160 are intersected (intersected in different layers), each gate line 150 and the gate electrodes 131 of the detection units 120 belonging to the same row are connected and are arranged on the same layer, and each data line 160 and the source electrodes 132 of the detection units 120 belonging to the same row are connected and are arranged on the same layer.

For example, in some examples, the gate line 150 may be located on the same layer as the corresponding gate electrode 131; the gate line 150 and the gate electrode 131 may also be formed by the same conductive layer through a patterning process. In this case, the gate line 150 and the electrode 140 are disposed in different layers.

For example, in some examples, the data line 160 may be located on the same layer as the corresponding source electrode 132; for example, the data line 160, the source electrode 132, and the drain electrode 133 may be formed by the same conductive layer through a patterning process. In this case, the data lines 160 and the gate lines 150 are disposed in different layers, and the data lines 160 and the electrode 140 are disposed in different layers.

For example, in some examples, as illustrated by FIGS. 1 and 2, the plurality of detection units 120 include stimulation units 121 and receiving units 122. The stimulation unit 121 is configured to apply a stimulation voltage, for example, to apply the stimulation voltage to the biological material to be detected through the electrode 140 of the stimulation unit 121; the receiving unit 122 is configured to receive an electrophysiological signal, for example, the electrode 140 of the receiving unit 122 receives the electrophysiological signal on the biological material to be detected. Therefore, the biological detection chip can achieve the electrical stimulation and impulse detection of the biological material to be detected through the stimulation unit and the receiving unit, respectively. It should be noted that one stimulation unit and one receiving unit may constitute a detection point, and the detection point corresponds to a position on the biological material to be detected, so that the electrical stimulation and the impulse detection may be performed simultaneously through the detection point on the position of the biological material to be detected; in addition, after the electrophysiological signal received by the receiving unit 122 can be transmitted to the data acquisition system through a corresponding data line, and is subjected to signal processing processes such as amplification, the processed electrophysiological signal can be recorded or analyzed.

For example, in some examples, as illustrated by FIG. 1, in the process of the electrical stimulation and impulse detection of the biological material to be detected, in order to avoid mutual interference between the applied stimulation voltage and the detected electrophysiological signal, the stimulation units 121 and the receiving units 122, which belong to the same column, can be driven by different data lines. That is, for the detection units 120 belonging to the same column, the data lines 160 may include a first data line 161 and a second data line 162, and the first data line 161 is connected to the source electrodes 132 of the receiving units 122 in the same column, and the second data line 162 is connected to the sources electrodes 132 of the stimulation units 121 in the same column. Of course, the embodiments of the present disclosure include, but are not limited thereto, the stimulation units 121 and the receiving units 122, which belong to the same column, may be driven by the same data line in a time-sharing driving manner.

For example, in some examples, in a case where the stimulation units 121 and the receiving units 122, which belong to the same column, can adopt different data lines, in order to avoid mutual interference of the signal on the first data line 161 and the signal on the second data line 162 and to facilitate the wiring of the first data line 161 and the second data line 162, the first data line 161 and the second data line 162 may be respectively disposed on two sides of the detection units 120 in the same column, that is, the first data line 161 may be disposed on a left side of the detection units 120 in the same column, and the second data line 162 may be disposed on a right side of the detection units 120 in the same column. In this case, in the column direction, the stimulation units 121 and the receiving units 122 are alternately disposed, and the thin film transistor 130 of the stimulation unit 121 is disposed corresponding to the first data line 161, and the thin film transistor 130 of the receiving unit 122 is disposed corresponding to the second data line 162.

For example, in some examples, as illustrated by FIG. 1, in the row direction, the stimulating units 121 and the receiving units 122 are alternately arranged, and one stimulation unit 121 and one receiving unit 122, which are adjacent, are axisymmetric with respect to a separation line between the one stimulation unit 121 and the one receiving unit 122, which are adjacent, which can be conducive to ameliorating the wiring of the first data line 161 and the second data line 162 and reducing the manufacturing difficulty of the biometric detection chip.

For example, in some examples, as illustrated by FIG. 1, in the row direction, the stimulation units 121 and the receiving units 122 are alternately arranged, and in the column direction, the stimulation units 121 and the receiving units 122 are alternately arranged. Two stimulation units 121 and two receiving units 122 constitute a detection point 125, in the detection point 125, the orthographic projections of the two stimulation units 121 on the first base substrate 110 and the orthographic projections of the two receiving units 122 on the first base substrate 110 form a 2*2 matrix. Thus, two stimulation units 121 and two receiving units 122 are provided in each detection point 125, and the two stimulation units 121 are distributed at two ends of a diagonal of the 2*2 matrix described above, so that in a case where the biological material to be detected does not completely cover the detection point 125, the two stimulation units 121 can stimulate the biological material to be detected on the detection point 125; in addition, the two receiving units 122 are distributed at two ends of the diagonal of the 2*2 matrix described above, so that the electrophysiological signal of the biological material to be detected on the detection point 125 can be detected by the two receiving units 122 in a case where the biological material to be detected does not completely cover the detection point 125.

Because the size of the area covered by the dendritic of a normal nerve cell is greater than 30 microns, and the width of the axon and myelin sheath is greater than 5 microns, in some examples, as illustrated by FIG. 1, the orthographic projection of the detection point 125 on the first base substrate 110 is substantially a rectangle, and a side length of the rectangle ranges from 4 to 6 microns. Therefore, the biological detection chip provided in this example can better match the size of the axon of the nerve cell, and thus can better achieve the flexible control of the electrical stimulation and impulsive signal capture position of the adherent nerve cells.

For example, in the detection point 125, the orthographic projection of the electrode 140 in each detection unit 120 on the first base substrate 110 may also be a rectangle, and the side length of the rectangle ranges from 1.5 to 2.5 microns. For example, the side length of the rectangle is approximately 2 microns. The distance between adjacent detection units 120 is approximately 1 micron.

For example, in some examples, the first base substrate 110 is made of a transparent insulating material, such as an inorganic material such as glass or quartz or an organic material such as polyvinyl chloride or polycarbonate. Therefore, in a case where the biological detection chip performs detection, it is conducive to observing the biological material to be detected using a device such as a microscope.

For example, in some examples, the electrode 140 may be made of a transparent metal oxide material, such as Indium Tin Oxide. Of course, the embodiments of the present disclosure include, but are not limited thereto, the electrode 140 may also be made of other materials, such as metal materials such as gold and platinum.

Figure 3:
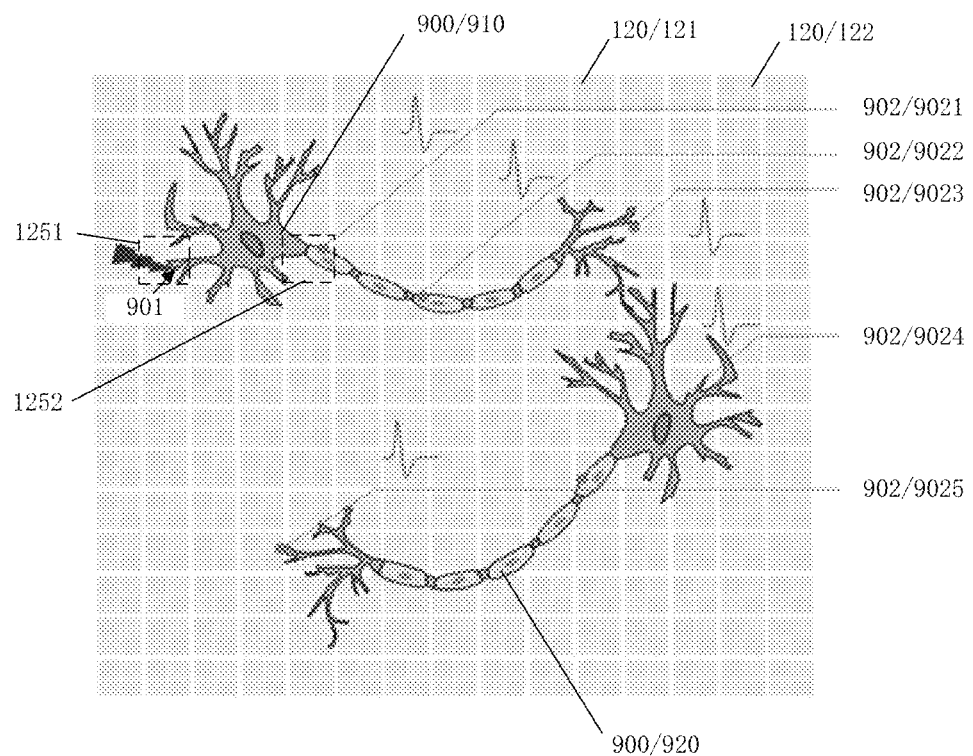
FIG. 3 is a schematic diagram of performing detection by a biological detection chip according to an embodiment of the present disclosure.

FIG. 3 is a schematic diagram of performing detection by a biological detection chip according to an embodiment of the present disclosure. As illustrated by FIG. 3, the biological material to be detected is nerve cells 900; the nerve cells 900 include a first nerve cell 910 and a second nerve cell 920. As illustrated by FIG. 3, the nerve cells 900 include a stimulation position 901 and a receiving position 902; the detection units 120 covered by the nerve cells 900 include a first detection point 1251 located at the stimulation position 901 of the nerve cells 900 and a second detection point 1252 located at the receiving position 902 of the nerve cells 900. Therefore, the electrical stimulation can be applied to the stimulation position 901 of the nerve cells 900 through the first detection point 1251; and the electrophysiological signal at the receiving position 902 of the nerve cells 900 can be received by the second detection point 1252, so that the electrical stimulation and impulse detection can be performed on the nerve cells. It should be noted that the above-mentioned receiving position is a position for detecting impulse, so the receiving position may include a plurality of positions at the same time. For example, as illustrated by FIG. 3, the receiving position 902 may include a first receiving position 9021, a second receiving position 9022, a third receiving position 9023, a fourth receiving position 9024, and a fifth receiving position 9025. In addition, the above-mentioned first detection point 1251 may be a single detection unit, or a detection point composed of one stimulation unit and one receiving unit, or a detection point composed of two stimulation units and two receiving units, the embodiments of the present disclosure include but are not limited thereto.

For example, as illustrated by FIG. 3, the stimulation position 901 may be a dendrite of the first nerve cell 910, and the receiving position 902 may be an axon or a myelin sheath (for example, the first receiving position 9021, the second receiving position 9022, and the third receiving position 9023) of the first nerve cell 910, or the axon or myelin (e.g., fourth receiving position 9024 and fifth receiving position 9025) of the second nerve cell 920.

Figure 4:
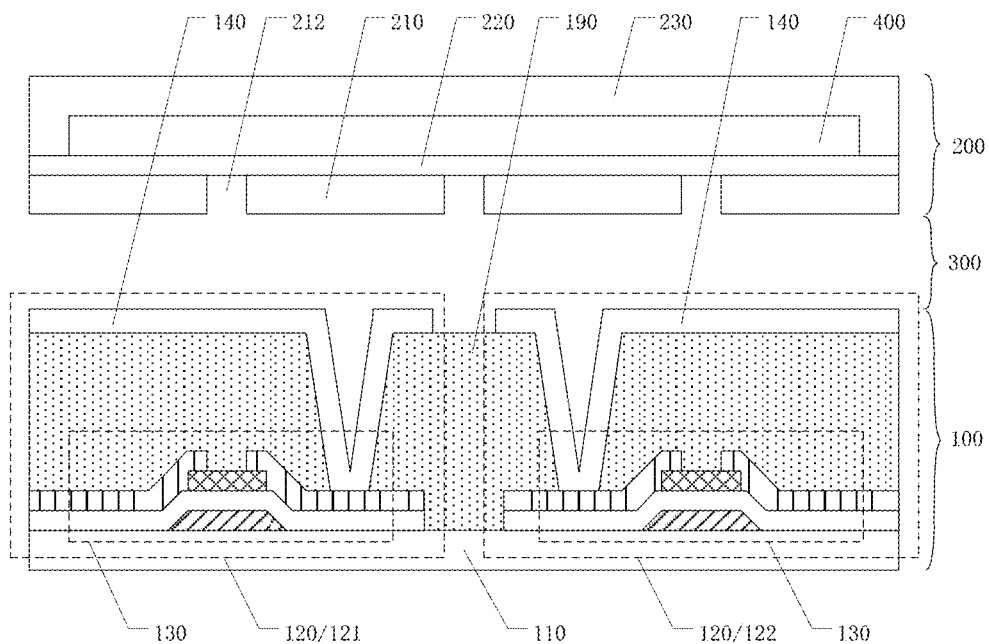
FIG. 4 is a schematic cross-sectional view of a biological detection device according to an embodiment of the present disclosure.

An embodiment of the present disclosure also provides a biological detection device. FIG. 4 is a schematic cross-sectional view of a biological detection device according to an embodiment of the present disclosure. As illustrated by FIG. 4, the biological detection device includes the biological detection chip provided by any one of the above embodiments. Therefore, the biological detection device can reduce the number and complexity of the routing of the plurality of detection units, thereby increasing the density of the plurality of detection units (the area for the routing in a unit area is reduced, and the density of the detection units can be increased), and furthermore achieving flexible control of electrical stimulation and impulse detection at different positions of the biological material to be detected and improving the accuracy of the detection. In addition, the biological detection device can also increase the effective area for culturing and detecting the biological material to be detected, and can avoid the electrical stimulation process of the biological material to be detected from interfering the gate lines and the data lines. For specific descriptions, reference may be made to the related descriptions of the biological detection chip.

For example, in some examples, as illustrated by FIG. 4, the biological detection device further includes an opposite substrate 200, which is cell-assembled with the biological detection chip 100 to form a culture cavity 300 between the biological detection chip 100 and the opposite substrate 200. The culture cavity 300 can be used for culturing the biological material to be detected, and provides certain life-sustaining conditions, thereby making the biological detection device more suitable for detecting and analyzing the biological materials.

For example, in a case where the biological material to be detected is a nerve cell, a phosphate buffer saline (PBS) can be added to the culture cavity. The PBS is the most widely used buffer solution in the biochemical research.

For example, the size of the culture cavity 300 in a direction perpendicular to the biological detection chip 100 is approximately 30 micrometers.

For example, in some examples, as illustrated by FIG. 4, the opposite substrate 200 includes a second base substrate 210, a breathable film 220, and a cover plate 230; the breathable film 220 is located on a side of the second base substrate 210 away from the biological detection chip 100, the cover plate 230 is located on a side of the breathable film 220 away from the second base substrate 210. The cover plate 230 and the breathable film 220 are spaced apart to form a gas channel 400 between the cover plate 230 and the breathable film 220. A vent hole 212 is formed in the second base substrate 210, and an orthographic projection of the vent hole 212 on the second base substrate 210 is located within an orthographic projection of the gas channel 400 on the second base substrate 210. Therefore, the vent hole 212 can introduce the gas in the gas channel 400 into the culture cavity 300. Thus, by adjusting the concentrations of different gases in the gas channel 400, the type and concentration of the gas in the culture cavity 300 can be controlled to detect the influence on the biological material to be detected under the gas. For example, in a case where the biological material to be detected is a nerve cell, the damage of the conduction ability of the nerve cell in a hypoxic environment can be detected by adjusting the concentration of oxygen in the gas channel 400.

For example, in some examples, the second base substrate 210 is made of a transparent insulating material, such as an inorganic material such as glass or quartz or an organic material such as polyvinyl chloride or polycarbonate. Therefore, in a case where the biological detection device performs detection, it is conducive to observing the biological material to be detected using a device such as a microscope.

For example, the vent hole 212 may be formed by an etching process.

For example, in some examples, the material of the breathable film 220 may include polydimethylsiloxane (PDMS), and the breathable film 220 is bonded to the second base substrate 210 through a plasma process.

Figure 5:
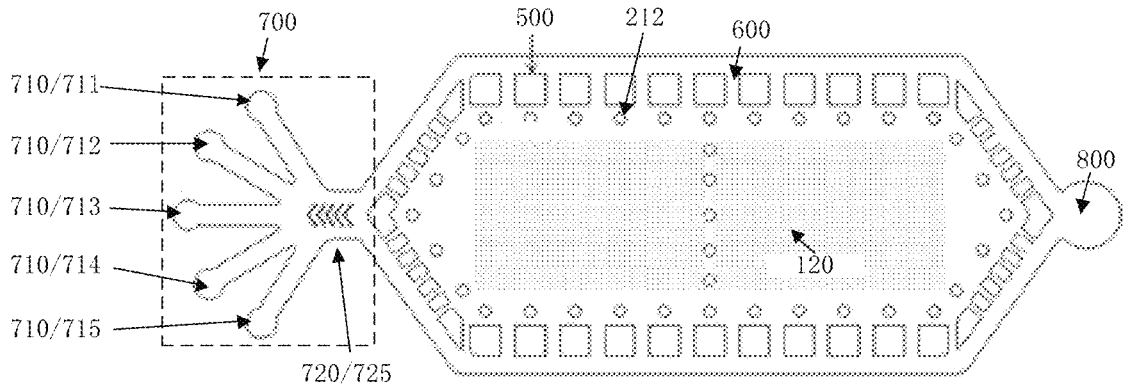
FIG. 5 is a schematic diagram of another biological detection device according to an embodiment of the present disclosure.

FIG. 5 is a schematic diagram of another biological detection device according to an embodiment of the present disclosure. As illustrated by FIG. 5, the biological detection device includes a plurality of support members 500, which are located between the biological detection chip 100 and the opposite substrate 200 and are disposed around the plurality of detection units 120. The plurality of support members 500 are disposed at intervals to form a liquid flow channel 600 that is between the adjacent support members 500 and is in communication with the culture cavity 300. Various liquid reagents, such as the aforementioned PBS, can be introduced into the culture cavity 300 through the liquid flow channel 600.

For example, the orthographic projection of the support member 500 on the second base substrate 210 may be a square with a side length of about 1 mm. The distance between adjacent support members 500 may range from 150 to 250 microns, such as 200 microns.

For example, in some examples, as illustrated by FIG. 5, the biological detection device further includes a reagent module 700 that communicates with the culture cavity 300 through the liquid flow channel 600. The reagent module 700 includes at least two reagent reservoirs 710 and a reagent mixing region 720; the at least two reagent reservoirs 710 are configured to store different types of detection reagents, and the reagent mixing region 720 is configured to mix different types of detection reagents.

For example, as illustrated by FIG. 5, the reagent module 700 includes five reagent reservoirs 710, and the five reagent reservoirs 710 includes a first reagent reservoir 711, a second reagent reservoir 712, a third reagent reservoir 713, a fourth reagent reservoir 714, and a fifth reagent reservoir 715. Any one of the five reagent reservoirs 710 can be used to add the PBS to the culture cavity 300, and the other reagent reservoirs 710 can be used to add other detection reagents.

For example, in a case where the biological material to be detected is a nerve cell, the PBS can be added to the culture cavity 300 through the first reagent reservoir 711, and then dopamine is added to the culture cavity 300 through the second reagent reservoir 712, thereby detecting the influence of the dopamine on the conduction ability of the nerve cell.

For example, the influences of different concentrations of dopamine on the conduction ability of nerve cell can be detected by controlling the ratio of dopamine and PBS. Of course, the detection reagents in the embodiments of the present disclosure include, but are not limited to dopamine, and the type and concentration of the specific detection reagent can be selected according to actual conditions.

For example, the reagent module may also be formed with two substrates facing each other, thereby forming the at least two reagent reservoirs and the reagent mixing region described above; in this case, the two substrates may be integrally formed with the biological detection chip and the opposite substrate, respectively. Of course, the embodiments of the present disclosure include, but are not limited thereto, the reagent module may also be a separate module, as long as the reagent module is in communication with the culture cavity through the liquid flow channel.

For example, in some examples, as illustrated by FIG. 5, the reagent mixing region 720 further includes a fish-bone mixing structure 725. Of course, the embodiments of the present disclosure include, but are not limited thereto, the reagent mixing region may also adopt other kinds of mixing structures.

For example, in some examples, as illustrated by FIG. 5, the biological detection device further includes a liquid outlet 800 for discharging the liquid in the culture cavity 300.

Figure 6:
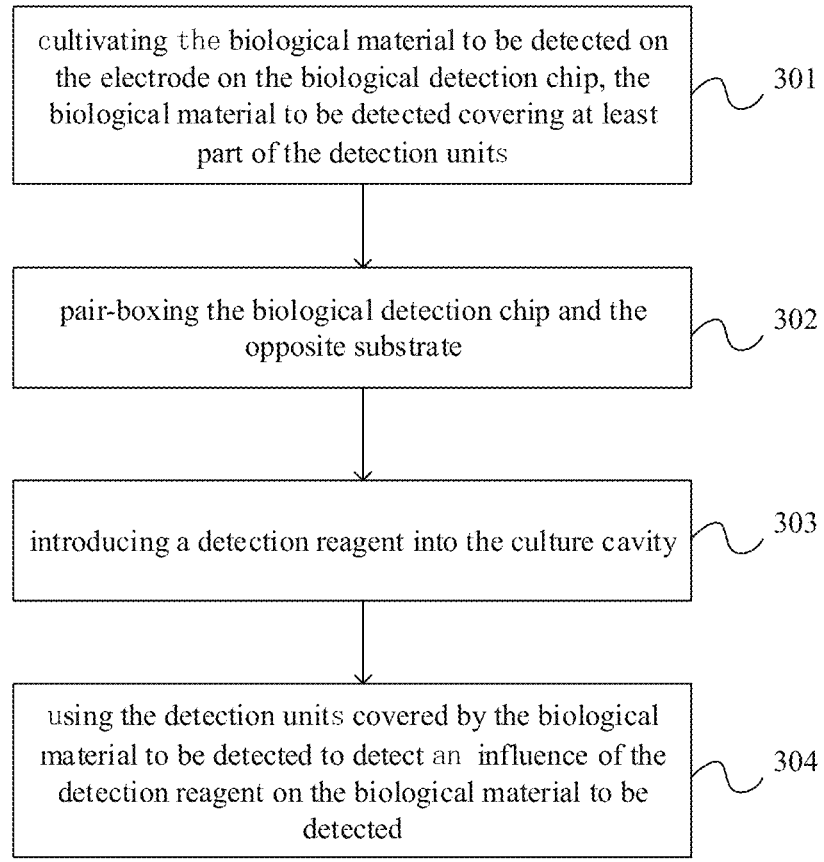
FIG. 6 is a flowchart of a biological detection method of a biological detection device according to an embodiment of the present disclosure.

An embodiment of the present disclosure also provides a biological detection method of a biological detection device. FIG. 6 is a flowchart of a biological detection method of a biological detection device according to an embodiment of the present disclosure. The biological detection device may also be any one of the biological detection devices described in the above embodiments. As illustrated by FIG. 6, the biological detection method includes the following steps S301-S304.

Step S301: cultivating the biological material to be detected on the electrode on the biological detection chip, the biological material to be detected covering at least part of the detection units.

For example, the biological material to be detected may be nerve cells; due to the randomness of adherent growth of nerve cells, the synaptic connection manners and growth positions of different nerve cells are very different; and the connection manner between nerve cells in each cell culture is also random. Therefore, the nerve cells cultured on the electrodes of the detection units arranged in an array will randomly cover at least part of the detection units. In this case, even if the adherent growth of nerve cells is random, the cultured nerve cells can be observed through a microscope or the like, and then the electrical stimulation and impulse detection are performed on the nerve cells through the detection units covered by the nerve cells.

Step S302: cell-assembling the biological detection chip and the opposite substrate.

For example, in a case where the biological material to be detected is a nerve cell, after the biological activity of the nerve cell is basically stable and communication between different nerve cells is established, the biological detection chip and the opposite substrate can be pair-boxed.

Step S303: introducing a detection reagent into the culture cavity.

For example, in a case where the biological material to be detected is a nerve cell, the PBS and other detection reagents, such as dopamine, can be added to the culture cavity to detect the influence of dopamine on the conduction ability of nerve cells. Of course, the detection reagents in the embodiments of the present disclosure include, but are not limited to dopamine, and the type and concentration of the specific detection reagent can be selected according to actual conditions.

Step S304: using the detection units covered by the biological material to be detected to detect an influence of the detection reagent on the biological material to be detected.

In the biological detection method provided by the embodiment of the present disclosure, a biological material to be detected may be cultured on an electrode on a biological detection chip, and then the detection units covered by the biological material to be detected is used to detect the influence of the detection reagent on the biological material to be detected. Because each detection unit includes a thin film transistor and an electrode, the plurality of detection units can be individually driven by the gate lines provided along the row direction and the data lines provided along the column direction, thereby reducing the number and complexity of routing of the plurality of detection units. Thus, the biological detection method can increase the density of the plurality of detection units (the area for routing in a unit area is reduced, and the density of the detection units can be increased), and furthermore achieve flexible control of electrical stimulation and impulse detection at different positions of the biological material to be detected. For example, in a case where the biological material to be detected is a nerve cell, if the density of the plurality of detection units increases, the number of detection units covered by the nerve cells increases, so that electrical stimulation and impulse detection can be performed on more positions of the nerve cells, thereby improving the accuracy of detection.

On the other hand, because the gate electrode, the source electrode and the drain electrode, and the electrode are located in different layers, the gate lines and the data lines for driving the plurality of detection units may be disposed at different layers from the electrode, and in this case, the orthographic projections of the gate lines and the data lines on the first base substrate is also close to or even overlapped with the orthographic projection of the electrode on the first base substrate. Thus, the biological detection method can further increase the density of the plurality of detection units (increasing the number of detection units per unit area), and further improve the degree of flexible control of electrical stimulation and impulse detection at different positions of the biological material to be detected (such as nerve cells). In addition, the biological detection method can also increase the effective area for culturing and detecting the biological material to be detected, and can avoid the electrical stimulation process of the biological material to be detected from interfering the gate lines and the data lines.

For example, detection reagents with different types and/or different concentrations can be introduced into the culture cavity, so that the detection units covered by the biological material to be detected can be used to detect the influence of the detection reagents with the different types and/or different concentrations on the biological material to be detected.

For example, in some examples, the detection units covered by the biological material to be detected include a first detection point located at a stimulation position of the biological material to be detected and a second detection point located at a receiving position of the biological material to be detected, using the detection units covered by the biological material to be detected to detect an influence of the detection reagent on the biological material to be detected comprises: applying electrical stimulation to the stimulation position of the biological material to be detected by the first detection point; and receiving an electrophysiological signal at the receiving position of the biological material to be detected by the second detection point. For a specific detection process, reference may be made to the related description of FIG. 3, and details are not described herein again.

For example, the first detection point may include at least one of the above-mentioned detection units, and the second detection point may include at least one of the above-mentioned detection units. That is, the above-mentioned first detection point may be a single detection unit, or a detection point formed by one stimulation unit and one receiving unit, or a detection point formed by two stimulation units and two receiving units. Embodiments of the present disclosure include but are not limited thereto.

For example, in some examples, the biological detection device may use a biological detection device as illustrated by FIG. 4. As illustrated by FIG. 4, in the biological detection device, the opposite substrate 200 includes: a second base substrate 210, a breathable film 220 located on a side of the second base substrate 210 away from the biological detection chip 110; and a cover plate 230 located on a side of the breathable film 220 away from the second base substrate 210. The cover plate 230 and the breathable film 220 are spaced apart to form a gas channel 400 between the cover plate 230 and the breathable film 220, and the second base substrate 210 is provided with a vent hole 212, and an orthographic projection of the vent hole 212 on the second base substrate 210 is located within an orthographic projection of the gas channel 400 on the second base substrate 210. Therefore, the vent hole 212 can introduce the gas in the gas channel 400 into the culture cavity 300. In this case, the biological detection method further includes: introducing gases (for example, gases of different types and/or different concentrations) into the gas channel; and detecting the influence of the gases on the biological material to be detected by using the detection units covered by the biological material to be detected.

For example, in a case where the biological material to be detected is a nerve cell, the damage of the conduction ability of the nerve cell in a hypoxic environment can be detected by adjusting the concentration of oxygen in the gas channel 400.

For example, in some examples, the detection units covered by the biological material to be detected include a first detection point located at a stimulation position of the biological material to be detected and a second detection point located at a receiving position of the biological material to be detected, and using the detection units covered by the biological material to be detected to detect the influence of the gas on the biological material to be detected comprises: applying electrical stimulation to the stimulation position of the biological material to be detected by the first detection point; and receiving an electrophysiological signal at the receiving position of the biological material to be detected by the second detection point. For a specific detection process, reference may be made to the related description of FIG. 3, and details are not described herein again.

For example, the first detection point may include at least one of the above-mentioned detection units, and the second detection point may include at least one of the above-mentioned detection units. That is, the above-mentioned first detection point may be a single detection unit, or a detection point formed by one stimulation unit and one receiving unit, or a detection point formed by two stimulation units and two receiving units. Embodiments of the present disclosure include but are not limited thereto. For example, in some examples, the biological detection method further includes: acquiring an image of the biological material to be detected on the biological detection chip; determining, according to the image, the detection units covered by the biological material to be detected and a positional relationship between the detection units and the biological material to be detected; determining the first detection point and the second detection point according to the positional relationship between each of the detection units and the biological material to be detected. For example, the image of the biological material to be detected on the biological detection device may be acquired through a microscope or an image sensor.

For example, in some examples, the biological material to be detected comprises at least one nerve cell, the stimulation position of the biological material to be detected comprises a dendrite of a nerve cell, and the receiving position of the biological material to be detected comprises an axon or a myelin sheath of a nerve cell at the stimulation position, or an axon or a myelin sheath of another nerve cell connected to the nerve cell at the stimulation position.

For example, the biological material to be detected is nerve cells; the nerve cells include a first nerve cell and a second nerve cell that are in communicate with each other. The nerve cells include a stimulation position and a receiving position; the stimulation position may be a dendrite of the first nerve cell, and the receiving position may be an axon or myelin sheath of the first nerve cell, or an axon or myelin sheath of the second nerve cell The following statements should be noted:

(1) The accompanying drawings involve only the structure(s) in connection with the embodiment(s) of the present disclosure, and other structure(s) can be referred to common design(s).

(2) In case of no conflict, features in one embodiment or in different embodiments can be combined.

What have been described above are only specific implementations of the present disclosure, the protection scope of the present disclosure is not limited thereto. Any modifications or substitutions easily occur to those skilled in the art within the technical scope of the present disclosure should be within the protection scope of the present disclosure. Therefore, the protection scope of the present disclosure should be based on the protection scope of the claims.

What is claimed is:

1. A biological detection chip, comprising:
   a first base substrate; and
   a plurality of detection units arranged in an array along a row direction and a column direction on the first base substrate;
   wherein each of the plurality of detection units comprises a thin film transistor and an electrode, the thin film transistor is on the first base substrate and comprises a gate electrode, a source electrode, and a drain electrode, and the electrode is on a side of the thin film transistor away from the first base substrate and is electrically connected to the drain electrode, and
   the electrode is configured to carry a biological material to be detected,
   the plurality of detection units comprise stimulation units and receiving units, each of the stimulation units is configured to apply a stimulation voltage through the electrode, and each of the receiving units is configured to receive an electrophysiological signal through the electrode, the biological detection chip further comprises: a plurality of gate lines; and a plurality of data lines arranged to intersect the plurality of gate lines, each of the plurality of gate lines and the gate electrodes of the detection units in a same row are connected and are on a same layer, and each of the plurality of data lines and the source electrodes of the detection units in a same column are connected and are on a same layer, the plurality of data lines comprise a first data line and a second data line, the first data line is connected with source electrodes of receiving units belonging to one column of detection units, and the second data line is connected with source electrodes of stimulation units belonging to the column of detection units, the first data line is disposed at a first side of the column of detection units, and the second data line is disposed at a second side of the column of detection units, the second side is opposite to the first side, and two adjacent columns of detection units are provided with one first data line and one second data line therebetween.

2. The biological detection chip according to claim 1, wherein, in the row direction, the stimulation units and the receiving units are alternately arranged, and one stimulation unit and one receiving unit, which are adjacent, are axisymmetric with respect to a separation line between the one stimulation unit and the one receiving unit, which are adjacent.

3. The biological detection chip according to claim 2, wherein, in the column direction, the stimulation units and the receiving units are alternately arranged, and two stimulation units and two receiving units constitute a detection point, and in the detection point, orthographic projections of the two stimulation units on the first base substrate and orthographic projections of the two receiving units on the first base substrate form a 2*2 matrix.

4. The biological detection chip according to claim 3, wherein an orthographic projection of the detection point on the first base substrate is substantially a rectangle, and a side length of the rectangle ranges from 4 to 6 microns.

5. The biological detection chip according to claim 1, wherein the electrode is directly connected to the drain electrode.

6. A biological detection device, comprising:
a biological detection chip; and
an opposite substrate, cell-assembled with the biological detection chip to form a culture cavity between the biological detection chip and the opposite substrate,
wherein the biological detection chip comprises:
a first base substrate; and
a plurality of detection units arranged in an array along a row direction and a column direction on the first base substrate;
wherein each of the plurality of detection units comprises a thin film transistor and an electrode, the thin film transistor is on the first base substrate and comprises a gate electrode, a source electrode, and a drain electrode, and the electrode is on a side of the thin film transistor away from the first base substrate and is electrically connected to the drain electrode, and
the electrode is configured to carry a biological material to be detected,
the plurality of detection units comprise stimulation units and receiving units, each of the stimulation units is configured to apply a stimulation voltage through the electrode, and each of the receiving units is configured to receive an electrophysiological signal through the electrode, the biological detection chip further comprises: a plurality of gate lines; and a plurality of data lines arranged to intersect the plurality of gate lines, each of the plurality of gate lines and the gate electrodes of the detection units in a same row are connected and are on a same layer, and each of the plurality of data lines and the source electrodes of the detection units in a same column are connected and are on a same layer, the plurality of data lines comprise a first data line and a second data line, the first data line is connected with source electrodes of receiving units belonging to one column of detection units, and the second data line is connected with source electrodes of stimulation units belonging to the column of detection units, the first data line is disposed at a first side of the column of detection units, and the second data line is disposed at a second side of the column of detection units, the second side is opposite to the first side, and two adjacent columns of detection units are provided with one first data line and one second data line therebetween.

7. The biological detection device according to claim 6, wherein the opposite substrate comprises:
a second base substrate;
a breathable film, on a side of the second base substrate away from the biological detection chip; and
a cover plate, on a side of the breathable film away from the second base substrate,
wherein the cover plate and the breathable film are spaced apart to form a gas channel between the cover plate and the breathable film, and the second base substrate is provided with a vent hole, and an orthographic projection of the vent hole on the second base substrate is located within an orthographic projection of the gas channel on the second base substrate.

8. The biological detection device according to claim 7, further comprising:
a plurality of support members, between the biological detection chip and the opposite substrate and surrounding the plurality of detection units,
wherein the plurality of support members are spaced apart to form a liquid flow channel that is between adjacent ones of the plurality of support members and in communication with the culture cavity.

9. The biological detection device according to claim 6, further comprising:
a plurality of support members, between the biological detection chip and the opposite substrate and surrounding the plurality of detection units,
wherein the plurality of support members are spaced apart to form a liquid flow channel that is between adjacent ones of the plurality of support members and in communication with the culture cavity.

10. The biological detection device according to claim 6, further comprising:
a reagent module, which is in communication with the culture cavity through the liquid flow channel,
wherein the reagent module comprises at least two reagent reservoirs and a reagent mixing region, the at least two reagent reservoirs are configured to store different types of detection reagents, and the reagent mixing region is configured to mix different types of detection reagents.

11. The biological detection device according to claim 10, wherein the reagent mixing region further comprises a fish-bone mixing structure.

12. A biological detection method of a biological detection device, wherein the biological detection device comprises a biological detection chip and an opposite substrate, cell-assembled with the biological detection chip to form a culture cavity between the biological detection chip and the opposite substrate, wherein the biological detection chip comprises:
- a first base substrate; and
- a plurality of detection units arranged in an array along a row direction and a column direction on the first base substrate;
- wherein each of the plurality of detection units comprises a thin film transistor and an electrode, the thin film transistor is on the first base substrate and comprises a gate electrode, a source electrode, and a drain electrode, and the electrode is on a side of the thin film transistor away from the first base substrate and is electrically connected to the drain electrode, and
- the electrode is configured to carry a biological material to be detected,
- the plurality of detection units comprise stimulation units and receiving units, each of the stimulation units is configured to apply a stimulation voltage through the electrode, and each of the receiving units is configured to receive an electrophysiological signal through the electrode,
- the biological detection chip further comprises: a plurality of gate lines; and a plurality of data lines arranged to intersect the plurality of gate lines,
- each of the plurality of gate lines and the gate electrodes of the detection units in a same row are connected and are on a same layer, and each of the plurality of data lines and the source electrodes of the detection units in a same column are connected and are on a same layer,
- the plurality of data lines comprise a first data line and a second data line, the first data line is connected with source electrodes of receiving units belonging to one column of detection units, and the second data line is connected with source electrodes of stimulation units belonging to the column of detection units,
- the first data line is disposed at a first side of the column of detection units, and the second data line is disposed at a second side of the column of detection units, the second side is opposite to the first side,
- two adjacent columns of detection units are provided with one first data line and one second data line therebetween, and
- the biological detection method comprises:
- cultivating the biological material to be detected on the electrode on the biological detection chip, the biological material to be detected covering at least part of the detection units;
- cell-assembling the biological detection chip and the opposite substrate;
- introducing a detection reagent into the culture cavity; and
- using the detection units covered by the biological material to be detected to detect an influence of the detection reagent on the biological material to be detected.

13. The biological detection method according to claim 12, wherein the opposite substrate comprises: a second base substrate; a breathable film, on a side of the second base substrate away from the biological detection chip; and a cover plate, on a side of the breathable film away from the second base substrate; the cover plate and the breathable film are spaced apart to form a gas channel between the cover plate and the breathable film, and the second base substrate is provided with a vent hole, and an orthographic projection of the vent hole on the second base substrate is located within an orthographic projection of the gas channel on the second base substrate;
the biological detection method further comprises:
introducing gas into the gas channel; and
using the detection units covered by the biological material to be detected to detect an influence of the gas on the biological material to be detected.

14. The biological detection method according to claim 13, wherein the detection units covered by the biological material to be detected comprises a first detection point located at a stimulation position of the biological material to be detected and a second detection point located at a receiving position of the biological material to be detected, and using the detection units covered by the biological material to be detected to detect the influence of the gas on the biological material to be detected comprises:
applying electrical stimulation to the stimulation position of the biological material to be detected by the first detection point; and
receiving an electrophysiological signal at the receiving position of the biological material to be detected by the second detection point,
wherein the first detection point comprises at least one of the detection units, and the second detection point comprises at least one of the detection units.

15. The biological detection method according to claim 12, wherein the detection units covered by the biological material to be detected comprise a first detection point located at a stimulation position of the biological material to be detected and a second detection point located at a receiving position of the biological material to be detected, and using the detection units covered by the biological material to be detected to detect the influence of the detection reagent on the biological material to be detected comprises:
applying electrical stimulation to the stimulation position of the biological material to be detected by the first detection point; and
receiving an electrophysiological signal at the receiving position of the biological material to be detected by the second detection point,
wherein the first detection point comprises at least one of the detection units, and the second detection point comprises at least one of the detection units.

16. The biological detection method according to claim 15, wherein the biological material to be detected comprises at least one nerve cell, the stimulation position of the biological material to be detected comprises a dendrite of a nerve cell, and the receiving position of the biological material to be detected comprises an axon or a myelin sheath of a nerve cell at the stimulation position, or an axon or a myelin sheath of another nerve cell connected to the nerve cell at the stimulation position.

17. The biological detection method according to claim 15, further comprising:
acquiring an image of the biological material to be detected on the biological detection chip;
determining, according to the image, the detection units covered by the biological material to be detected and a positional relationship between the detection units and the biological material to be detected; and determining the first detection point and the second detection point according to the positional relationship between each of the detection units and the biological material to be detected.

* * * * *